US010206554B2

(12) United States Patent
Mizuno

(10) Patent No.: US 10,206,554 B2
(45) Date of Patent: Feb. 19, 2019

(54) IMAGE PICKUP SYSTEM WITH WHITE SPOT CORRECTION

(71) Applicant: OLYMPUS CORPORATION, Tokyo (JP)

(72) Inventor: Kyosuke Mizuno, Hino (JP)

(73) Assignee: Olympus Corporation, Tokyo (JP)

( * ) Notice: Subject to any disclaimer, the term of this patent is extended or adjusted under 35 U.S.C. 154(b) by 43 days.

(21) Appl. No.: 15/378,145

(22) Filed: Dec. 14, 2016

(65) Prior Publication Data

US 2017/0086649 A1 Mar. 30, 2017

Related U.S. Application Data

(63) Continuation of application No. PCT/JP2015/078091, filed on Oct. 2, 2015.

(30) Foreign Application Priority Data

Oct. 14, 2014 (JP) .................................. 2014-210281

(51) Int. Cl.
*A61B 1/04* (2006.01)
*H04N 5/367* (2011.01)
(Continued)

(52) U.S. Cl.
CPC ........ *A61B 1/00009* (2013.01); *A61B 1/0002* (2013.01); *A61B 1/00045* (2013.01);
(Continued)

(58) Field of Classification Search
CPC .............. A61B 1/00009; A61B 1/0002; A61B 1/00193; A61B 1/045; G02B 23/2415;
(Continued)

(56) References Cited

U.S. PATENT DOCUMENTS 6,529,640 B1 3/2003 Utagawa et al.
6,987,534 B1 * 1/2006 Seta .................. G01S 11/12
348/229.1

(Continued)

FOREIGN PATENT DOCUMENTS

JP H10-322603 A 12/1998
JP H11-355650 A 12/1999
(Continued)

OTHER PUBLICATIONS

Partial Supplementary European Search Report dated Dec. 15, 2017 in European Patent Application No. 15 85 1024.8.
(Continued)

*Primary Examiner* — John P Leubecker
(74) *Attorney, Agent, or Firm* — Scully, Scott, Murphy & Presser, P.C.

(57) ABSTRACT

An image pickup system including an optical system configured to generate a first optical image and a second optical image having disparity, of an object, includes a storage unit configured to store in advance image formation position information and disparity information of the first optical image and the second optical image, and an image processing unit configured to generate a first image signal and a second image signal for display by respectively cutting out a first region corresponding to the first optical image and a second region corresponding to the second optical image, and the image processing unit includes a luminance value comparing unit configured to compare luminance values of respective pixels in the first image signal and the second image signal, and a detecting unit configured to detect a pixel defect based on the comparison result of the luminance value comparing unit.

3 Claims, 7 Drawing Sheets

(51) Int. Cl.
*A61B 1/00* (2006.01)
*G02B 23/24* (2006.01)
*H04N 5/225* (2006.01)
*H04N 5/232* (2006.01)
*A61B 1/045* (2006.01)
*H04N 13/20* (2018.01)

(52) U.S. Cl.
CPC ............ *A61B 1/00193* (2013.01); *A61B 1/04* (2013.01); *A61B 1/045* (2013.01); *G02B 23/24* (2013.01); *G02B 23/2415* (2013.01); *G02B 23/2484* (2013.01); *H04N 5/225* (2013.01); *H04N 5/2253* (2013.01); *H04N 5/2254* (2013.01); *H04N 5/2256* (2013.01); *H04N 5/232* (2013.01); *H04N 5/367* (2013.01); *H04N 13/20* (2018.05); *H04N 2005/2255* (2013.01)

(58) Field of Classification Search
CPC ....... G02B 23/2484; H04N 2005/2255; H04N 5/2351; H04N 5/367
See application file for complete search history.

(56) References Cited

U.S. PATENT DOCUMENTS

| | | | |
|---|---|---|---|
| 2007/0035618 A1 | 2/2007 | Yoshida | |
| 2013/0038698 A1* | 2/2013 | Yoshida | G06K 9/6203 348/47 |
| 2013/0041220 A1* | 2/2013 | Kutsuma | A61B 1/00009 600/109 |
| 2013/0063572 A1* | 3/2013 | Ramachandra | H04N 13/122 348/47 |
| 2014/0002675 A1 | 1/2014 | Duparre et al. | |
| 2014/0219575 A1 | 8/2014 | Govindarao et al. | |
| 2016/0174818 A1* | 6/2016 | Viering | A61B 1/00009 600/109 |
| 2016/0277694 A1* | 9/2016 | Lee | H04N 5/367 |
| 2018/0040135 A1* | 2/2018 | Mullis | H04N 5/247 |

FOREIGN PATENT DOCUMENTS

| | | |
|---|---|---|
| JP | 2001-086411 A | 3/2001 |
| JP | 2001-148865 A | 5/2001 |
| JP | 2003-032559 A | 1/2003 |
| JP | 2004-313523 A | 11/2004 |
| JP | 2005-311983 A | 11/2005 |
| JP | 2006-086839 A | 3/2006 |
| JP | 2009-232200 A | 10/2009 |
| JP | 2012-065204 A | 3/2012 |
| JP | 2014-007599 A | 1/2014 |

OTHER PUBLICATIONS

International Search Report dated Dec. 1, 2015 issued in PCT/JP2015/078091.

Japanese Office Action dated Jun. 7, 2016 issued in Japanese Patent Application No. 2016-522076.

* cited by examiner

IMAGE PICKUP SYSTEM WITH WHITE SPOT CORRECTION

CROSS REFERENCE TO RELATED APPLICATION

This application is a continuation application of PCT/JP2015/078091 filed on Oct. 2, 2015 and claims benefit of Japanese Application No. 2014-210281 filed in Japan on Oct. 14, 2014, the entire contents of which are incorporated herein by this reference.

BACKGROUND OF THE INVENTION

1. Field of the Invention

The present invention relates to an image pickup system, and more particularly, to an image pickup system which can generate a new image for display using two types of images and detect a white spot pixel.

2. Description of the Related Art

Conventionally, in an image pickup system including a solid-state image pickup device, there is a case where a pixel defect referred to as a so-called white spot occurs based on a crystal defect on an image pickup surface of the solid-state image pickup device. Because it is difficult to completely remove such a pixel defect, conventionally, efforts have been made to improve a yield ratio of the solid-state image pickup device by providing a pixel defect correction circuit and correcting an image.

For example, Japanese Patent Application Laid-Open Publication No. 10-322603 discloses a technique of detecting a defect pixel of a solid-state image pickup device using a pixel defect inspection apparatus when an image pickup system is shipped from the factory, recording position information of the defect pixel, and, then, correcting the pixel defect based on the recorded position information of the defect pixel.

Further, also in an endoscope system on which a solid-state image pickup device is mounted, conventionally, a technique of detecting and recording a white spot pixel and correcting the white spot based on the recorded information has been known.

Specifically, in a step of shipping an endoscope system from the factory, a white spot pixel is detected by picking up an image of a black object and determining an excess luminance value, and storing a position of the white spot pixel in an ID memory, or the like, mounted on an endoscope as address information of XY. Then, a technique is known in which, when the endoscope is used, predetermined correction processing is performed on the white spot pixel based on the address information stored in the ID memory at a connected processor or at the endoscope itself.

However, while the above-described correction of the white spot pixel effectively works on a pixel defect such as a white spot (white spot generated previously) which has been already generated upon shipping from the factory, it is difficult for the above-described correction to effectively work on a white spot pixel generated after shipment.

That is, it is known that a white spot pixel degrades over time because the white spot pixel is based on a crystal defect, or tends to increase in accordance with increase of the temperature. However, because the conventional detection of a defect pixel such as detection of a white spot is performed during a manufacturing stage as described above, the conventional detection cannot cope with change over time, or the like, of a defect pixel, which occurs later in the market after shipping.

As a technique for coping with change over time of a pixel defect after shipping from the factory, Japanese Patent Application Laid-Open Publication No. 2001-086411 discloses a technique of displacing an image formation position of light incident on a solid-state image pickup device by moving an optical member inserted into an optical path of an image pickup optical system, and detecting a pixel defect by comparing image data before and after a frame.

Further, Japanese Patent Application Laid-Open Publication No. 2009-232200 discloses a pixel defect correcting method of respectively picking up images of a plurality of dispersed light obtained by dispersing image pickup light, comparing video signals outputted by picking up images at the same image pickup position or the near image pickup position for each of the respective dispersed light, detecting whether or not a pixel defect occurs at the image pickup device which picks up an image of any of the dispersed light according to a comparison result, and performing correction.

On the other hand, conventionally, in an image pickup system which can acquire two types of images, a technique of generating a new image for display using the two types of images is put to practical use.

For example, as a technique of generating a stereo image using two types of picked up images having disparity, Japanese Patent Application Laid-Open Publication No. 2012-065204 and Japanese Patent Application Laid-Open Publication No. 2001-148865 disclose an image pickup apparatus which picks up a stereo image (3D image) using a plurality of image pickup units.

Further, Japanese Patent Application Laid-Open Publication No. 2003-032559 discloses a technique of generating an image for display having a high dynamic range using two types of picked up images having different luminance.

In the technique disclosed in Japanese Patent Application Laid-Open Publication No. 2003-032559, one optical image is separated into two optical images by a light flux separating unit, and these two separated optical images are formed on an image pickup surface of one image pickup device. In this technique, two image pickup signals having different luminance are generated by performing photoelectric conversion on the two types of optical images on the image pickup device, and a high dynamic range image is acquired by converting the two image pickup signals into image signals and synthesizing the image signals.

SUMMARY OF THE INVENTION

An image pickup system according to one aspect of the present invention includes an image pickup unit configured to pick up an optical image of an object, an optical system configured to generate a first optical image of the object and a second optical image having first light disparity and form the first optical image and the second optical image at predetermined positions on the image pickup unit, a storage unit configured to store in advance image formation position information of the first optical image and the second optical image on an image pickup surface of the image pickup unit and disparity information of the first optical image and the second optical image, an image pickup signal generating unit configured to perform photoelectric conversion on the first optical image and the second optical image formed on the image pickup unit to respectively output the first optical image and the second optical image as a first image pickup signal and a second image pickup signal, and an image processing unit configured to generate a first image signal and a second image signal for display by respectively cutting out a first region corresponding to the first optical image and a second region corresponding to the second optical image on the image pickup surface based on the image formation position information, and the image processing unit includes a disparity adjusting unit configured to set a pair of pixel positions indicating corresponding regions of the first image signal and the second image signal based on the disparity information, a luminance value comparing unit configured to compare luminance values of respective pixels in the first image signal and the second image signal based on setting of the disparity adjusting unit, and a detecting unit configured to detect a pixel defect based on a comparison result of the luminance value comparing unit.

Further, an image pickup system according to another aspect of the present invention includes an image pickup unit configured to pick up an optical image of an object, an optical system configured to generate a first optical image of the object and a second optical image having different brightness from brightness of the first optical image and form the first optical image and the second optical image at predetermined positions on the image pickup unit, a storage unit configured to store in advance image formation position information of the first optical image and the second optical image on an image pickup surface of the image pickup unit and luminance difference information of the first optical image and the second optical image, an image pickup signal generating unit configured to perform photoelectric conversion on the first optical image and the second optical image formed on the image pickup unit to respectively output the first optical image and the second optical image as a first image pickup signal and a second image pickup signal, and an image processing unit configured to generate a first image signal and a second image signal for display by respectively cutting out a first region corresponding to the first optical image and a second region corresponding to the second optical image on the image pickup surface based on the image formation position information, and the image processing unit includes a luminance difference adjusting unit configured to set a pair of pixel positions indicating corresponding regions of the first image signal and the second image signal based on the luminance difference information, a luminance value comparing unit configured to compare luminance values of respective pixels in the first image signal and the second image signal based on setting of the luminance difference adjusting unit, and a detecting unit configured to detect a pixel defect based on a comparison result of the luminance value comparing unit.

DETAILED DESCRIPTION OF THE PREFERRED EMBODIMENT(S)

Preferred embodiments of the present invention will be described below with reference to the drawings. Note that, in each drawing used for the following description, in order to make each component have a size which can be recognized on the drawings, a scale size is made different for each component, and the number of components, the shape of components, a ratio of sizes of the components and relative positional relationship of the components of the present invention are not limited to those illustrated in these drawings.

(First Embodiment)

Figure 1:
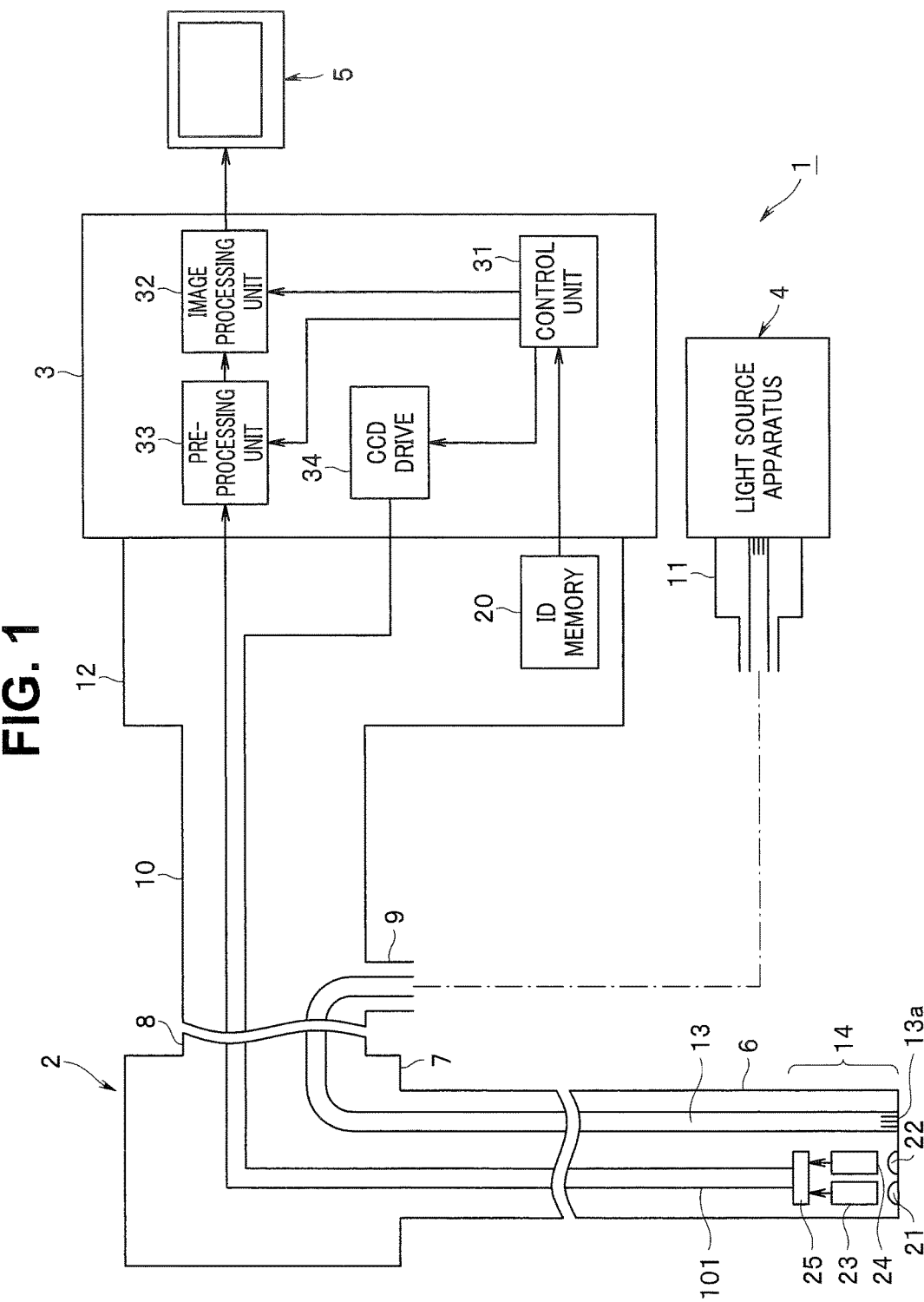
FIG. 1 is a diagram illustrating a configuration of an endoscope system according to a first embodiment of the present invention.
Figure 2:
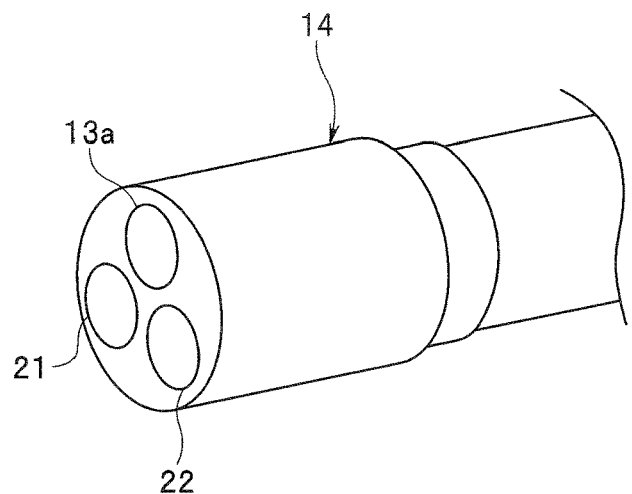
FIG. 2 is a perspective view illustrating a configuration of a distal end portion of an insertion portion in the endoscope system according to the first embodiment.
Figure 3:
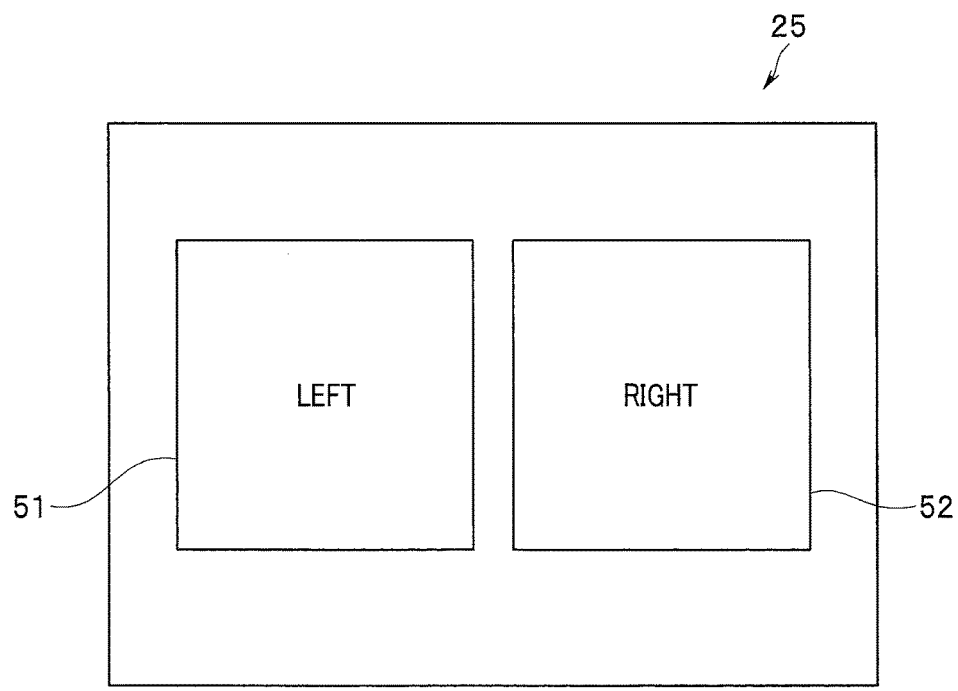
FIG. 3 is a diagram illustrating an example of two types of optical images formed on an image pickup device in the endoscope system according to the first embodiment.

A configuration of an endoscope system according to a first embodiment will be described using FIG. 1 to FIG. 3. FIG. 1 is a diagram illustrating a configuration of an endoscope system according to the first embodiment of the present invention. FIG. 2 is a perspective view illustrating a configuration of a distal end portion of an insertion portion in the endoscope system according to the first embodiment, and FIG. 3 is a diagram illustrating an example of two types of optical images formed on an image pickup device in the endoscope system according to the first embodiment.

As illustrated in FIG. 1, the endoscope system 1 according to the first embodiment of the present invention includes an endoscope 2 which is a so-called 3D endoscope having an image pickup device 25 and configured to generate a stereo image, a processor 3 to which the endoscope 2 is detachably connected and configured to perform predetermined signal processing, a light source apparatus 4 to which the endoscope 2 is detachably connected and configured to supply illumination light to the endoscope 2, and a monitor 5 as a display apparatus configured to display an image signal generated by the processor 3 as an endoscope image.

The endoscope 2 includes an elongated insertion portion 6 to be inserted into a body cavity, an operation portion 7 provided at a rear end of the insertion portion 6, and a universal cord 8 extending from the operation portion 7. The universal cord 8 diverges into a light guide cord 9 and a signal cord (signal cable) 10 near the proximal end or in midstream.

A connector 11 for light source at an end portion of the light guide cord 9 is detachably connected to the light source apparatus 4, and a connector 12 for signal at an end portion of the signal cord 10 is detachably connected to the processor 3.

Further, at the connector 12 for signal, an ID memory 20 is disposed, which is a storage unit which stores individual information for each endoscope 2, for example, individual information relating to the image pickup device 25.

A light guide 13 which transmits illumination light is inserted into the insertion portion 6, the operation portion 7 and the universal cord 8. By connecting the connector 11 for light source to the light source apparatus 4, the illumination light from the light source apparatus 4 is transmitted by the light guide 13, and the transmitted illumination light is emitted from a light guide distal end surface 13a attached to an illumination window provided at the distal end portion 14 of the insertion portion 6.

Note that it is also possible to employ a configuration where a connector in which the connector 11 for light source and the connector 12 for signal are integrated is connected to the light source apparatus 4, and a signal of the connector 12 for signal is exchanged with the processor 3 using a cable which connects the light source apparatus 4 with the processor 3.

An observation window (image pickup window) is provided adjacent to the illumination window at the distal end portion 14, and two objective lenses of a first objective lens 21 and a second objective lens 22 which receive entrance of light of optical images of an illuminated object such as an affected area so as to have disparity from each other are disposed at the observation window (see FIG. 2).

Behind the first objective lens 21 and the second objective lens 22, predetermined objective optical systems 23 and 24 are respectively disposed. Through the objective optical systems 23 and 24, the image pickup device 25 is disposed at an image formation position of the first objective lens 21 and the second objective lens 22.

That is, as illustrated in FIG. 2, the endoscope 2 according to the first embodiment receives input of optical images having disparity from each other at the two objective lenses of the first objective lens 21 and the second objective lens 22 as a 3D endoscope, generates a first optical image and a second optical image which are separate optical images at the respective objective optical systems 23 and 24, and, as illustrated in FIG. 1, forms these separate optical images on the image pickup surface of one image pickup device 25.

The image pickup device 25 is configured with, for example, a CCD image sensor, and is connected to the processor 3 through a cable inserted into the insertion portion 6 and the universal cord 8 and via the connector 12 for signal.

Further, as described above, in the present embodiment, the image pickup device 25 forms the first optical image and the second optical image which are separate optical images in predetermined regions corresponding to the respective optical images on the same image pickup surface of the CCD.

For example, as illustrated in FIG. 3, the first optical image for left is formed in a first region 51, and the second optical image for right is knitted in a second region 52.

Note that, while, in FIG. 3, the first region 51 and the second region 52 have substantially rectangular shape, this is because the regions are made to correspond to regions when cut out as predetermined image pickup regions relating to the first optical image and the second optical image at the processor 3.

Therefore, the shape of the first region 51 and the second region 52 which are respective image formation regions of the first optical image and the second optical image is not limited to the rectangular shape, and, for example, may be circular shape. Further, the first region 51 and the second region 52 may be set so that the regions overlap with each other partially.

In the endoscope system according to the first embodiment, for example, during an inspection step in an endoscope manufacturing step, "image formation position information" indicating positions (regions) on the image pickup surface of the image pickup device 25 where the two optical images are formed is acquired in advance through inspection for each endoscope to be shipped, and the "image formation position information" is stored in the ID memory 20 disposed at the connector 12 for signal.

This position information is, for example, X-Y coordinate information on the image pickup surface, of the first region 51 corresponding to the first optical image for left and the second region 52 corresponding to the second optical image for right as illustrated in FIG. 3.

Further, in the first embodiment, "disparity information" of the first optical image for left and the second optical image for right, relating to the image pickup device 25 is stored in the ID memory 20.

The processor 3 includes a power supply circuit which is configured to generate power supplies of a plurality of power supply voltages required for operation of the image pickup device, or the like, and which is not illustrated, a signal processing circuit (such as an image processing unit 32 and a pre-processing unit 33) configured to perform predetermined signal processing on the image pickup signal outputted from the image pickup device, a CCD drive circuit 34 configured to drive the image pickup device 25 in the endoscope 2, and a control unit 31 configured to control various kinds of circuits including the power supply circuit, the signal processing circuit and the CCD drive circuit 34.

As described above, the control unit 31 controls various kinds of circuits within the processor 3 and acquires the "image formation position information" which is individual information of the endoscope 2 stored in the ID memory 20 of the connector 12 for signal when the endoscope 2 is connected to the processor 3.

The pre-processing unit 33 which receives input of the image pickup signals (in the present embodiment, image pickup signals relating to the first optical image and the second optical image) from the image pickup device 25 and performs predetermined pre-signal processing, is configured with a publicly known signal amplifying unit, a process circuit, an A/D converter, a white balance circuit, or the like, and is controlled by the control unit 31.

The image processing unit 32 includes an image processing unit which is configured to perform predetermined image processing on an output signal from the pre-processing unit 33 and which is not illustrated, and an image pickup region cut out unit which is configured to cut out predetermined image pickup regions for the first optical image and the second optical image based on the "image formation position information" stored in the ID memory 20 under control of the control unit 31, and which is not illustrated.

The image pickup region cut out unit respectively cuts out the first region 51 corresponding to the first optical image and the second region 52 corresponding to the second optical image on the image pickup surface based on the "image formation position information" of the first optical image and the second optical image formed on the image pickup surface of the image pickup device 25, which is individual information of the endoscope 2 connected to the processor 3.

The image processing unit 32 performs predetermined image processing respectively on the two image pickup regions (the first region 51 and the second region 52) cut out at the image pickup region cut out unit to generate two image signals for display (in the present embodiment, a left side image signal relating to the first region 51 and a right side image signal relating to the second region 52).

(White Spot Detection and Correction Function in the First Embodiment)

Further, the image processing unit 32 has a function of detecting a white spot in the image pickup device 25 based on the left side image signal relating to the first region 51 and the right side image signal relating to the second region 52 and correcting the white spot.

The white spot detection and correction function in the present embodiment will be described below.

Figure 4:
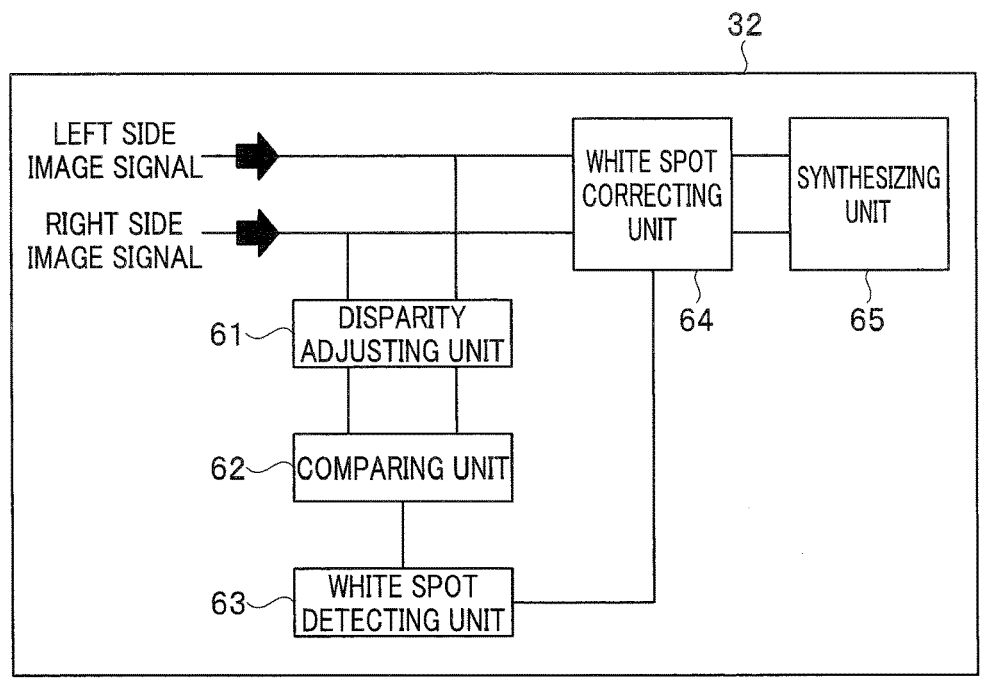
FIG. 4 is a block diagram illustrating a configuration of function units which detect and correct a white spot in an image processing unit of the endoscope system according to the first embodiment.

FIG. 4 is a block diagram illustrating a configuration of function units which detect and correct a white spot in the image processing unit of the endoscope system according to the first embodiment.

As illustrated in FIG. 4, the image processing unit 32 includes a disparity adjusting unit 61 configured to adjust a value of disparity of the left side image signal and the right side image signal which are two image signals having different optical characteristics (in the present embodiment, that is, having disparity), a comparing unit 62 configured to compare luminance values of the left side image signal and the right side image signal adjusted at the disparity adjusting unit 61, a white spot detecting unit 63 configured to detect a white spot on the image pickup device 25 based on information compared at the comparing unit 62, and a white spot correcting unit 64 configured to perform predetermined correction on a pixel where the white spot occurs based on a detection result at the white spot detecting unit 63.

The disparity adjusting unit 61 stores the "disparity information" stored in the ID memory 20 in the endoscope 2 connected to the processor 3 under control of the control unit 31, and performs adjustment so that disparity between the left side image signal relating to the first region 51 and the right side image signal relating to the second region 52 having disparity becomes substantially zero based on this disparity information.

Specifically, in the present embodiment, adjustment is performed so that the disparity becomes substantially zero by displacing a visual direction relating to the left side image signal by an amount corresponding to the disparity so as to match a visual direction relating to the right side image signal.

The comparing unit 62 compares a luminance value of each pixel in the left side image signal relating to the first region 51 for which the disparity is adjusted to be substantially zero at the disparity adjusting unit 61 and a luminance value of each pixel in the right side image signal relating to the second region 52 for each pixel under control of the control unit 31.

The white spot detecting unit 63 detects whether or not there is a white spot on the image pickup device 25 based on the comparison result of the luminance value for each pixel in the first region 51 and the second region 52 compared at the comparing unit 62 under control of the control unit 31.

Figure 5:
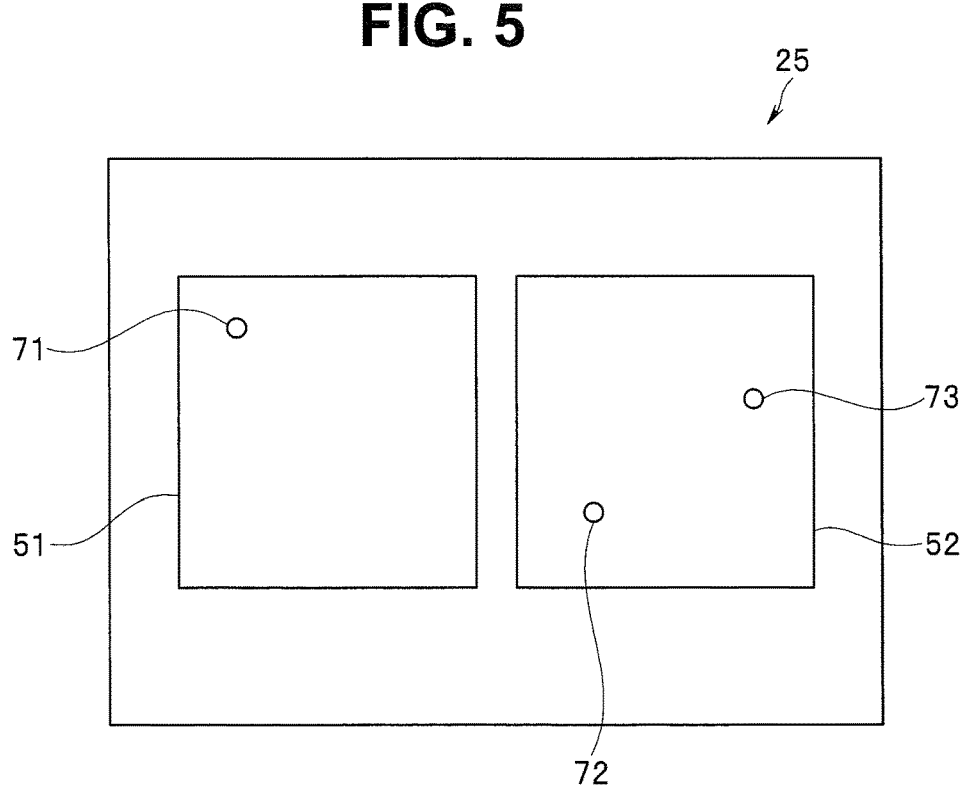
FIG. 5 is a diagram illustrating aspect when a white spot occurs at the image pickup device in the endoscope system according to the first embodiment.

Specifically, as illustrated in FIG. 5, as a result of the comparison at the comparing unit 62, for example, when a pixel 71 in the first region 51 has a luminance value greater than that of the corresponding pixel in the second region 52 by equal to or greater than a predetermined value, the white spot detecting unit 63 determines that a white spot occurs at a portion of the pixel 71.

In a similar manner, when a pixel 72 and a pixel 73 in the second region 52 have luminance values greater than those of corresponding pixels in the first region 51 by equal to or greater than a predetermined value, the white spot detecting unit 63 determines that white spots occur at portions of the pixel 72 and the pixel 73.

The white spot correcting unit 64 performs predetermined correction on the pixels where the white spots occur, in the above-described case, the pixels 71, 72 and 73, based on the detection result at the white spot detecting unit 63 so as to reduce influence of the white spots.

Figure 6:
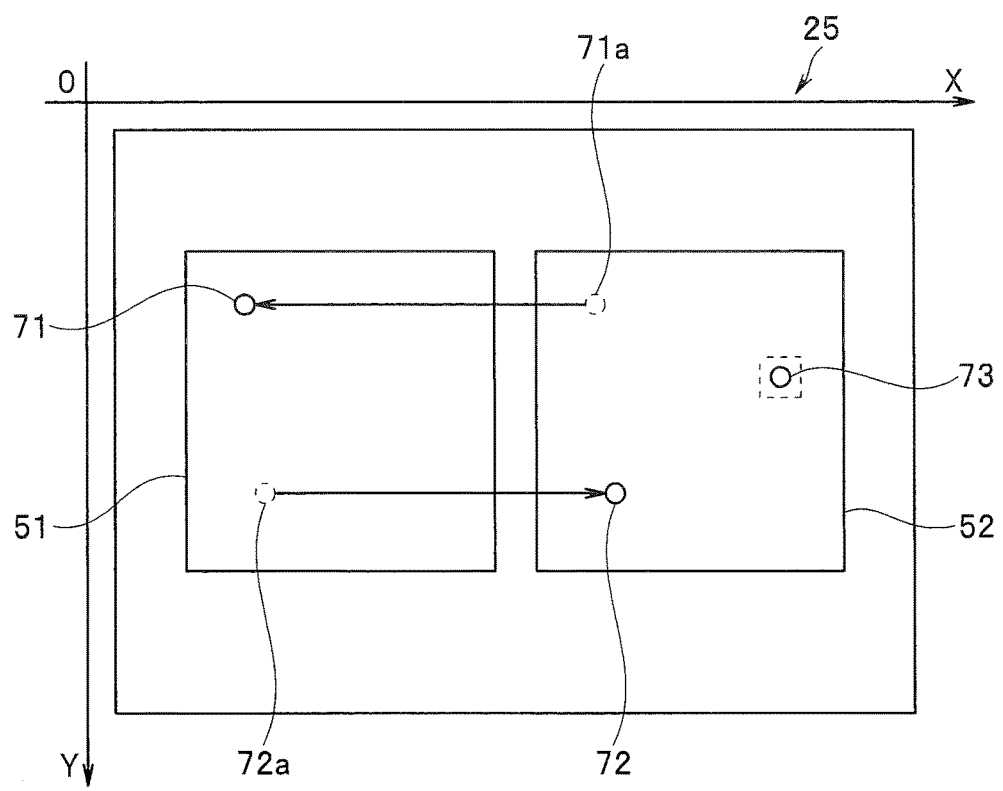
FIG. 6 is a diagram illustrating aspect when a white spot occurring at the image pickup device is corrected in the endoscope system according to the first embodiment.

For example, as illustrated in FIG. 6, correction is performed by replacing an output signal relating to the pixel 71 in the first region 51 where the white spot occurs with an output signal relating to the corresponding pixel 71a in the second region 52. Further, in a similar manner, correction is performed by replacing an output signal relating to the pixel 72 in the second region 52 where the white spot occurs with an output signal relating to the corresponding pixel 72a in the first region 51.

On the other hand, as illustrated in FIG. 6, as in the pixel 73 where the white spot occurs, correction may be performed by performing complementation based on information of surrounding pixels.

Returning to FIG. 4, the image processing unit 32 includes a synthesizing unit 65 configured to perform predetermined 3D synthesis processing on the left side image signal and the right side image signal for which the white spots are corrected at the white spot correcting unit 64 and output the synthesized signal, and outputs one video signal subjected to 3D synthesis processing at the synthesizing unit 65 to the monitor 5.

Note that, while, in the present embodiment, as described above, predetermined 3D synthesis processing is performed on the image pickup signals corresponding to the two image pickup regions at the image processing unit 32, and the result is outputted to a normal monitor as one video signal, the present invention is not limited to this, and, it is also possible to employ a so-called 3D compatible monitor apparatus as the monitor 5, and perform publicly known 3D processing as appropriate on the two video signals having disparity without performing the above-described synthesis processing and display the result.

Operation of the endoscope system according to the first embodiment will be described next.

First, in the endoscope 2, as described above, in an inspection step of an endoscope manufacturing step, "image formation position information" indicating positions (regions) on the image pickup surface of the image pickup device 25 where the two optical images are formed is acquired in advance through inspection for each endoscope to be shipped, and the "image formation position information" is stored in the ID memory 20 disposed at the connector 12 for signal.

Further, in the first embodiment, in the inspection step of the endoscope manufacturing step, "disparity information" of the first optical image for left and the second optical image for right at the endoscope 2 is stored in the ID memory 20.

Then, at the processor 3, when the endoscope 2 is connected to the processor 3, the control unit 31 acquires the "image formation position information" and the "disparity information" stored in the ID memory 20.

On the other hand, at the processor 3, the pre-processing unit 33 receives input of the image pickup signal from the image pickup device 25 and performs predetermined pre-processing under control of the control unit 31, and the image pickup region cut out unit in the image processing unit 32 cuts out predetermined image pickup regions for the first optical image and the second optical image based on the "image formation position information".

Then, the image processing unit 32 performs predetermined image processing respectively on the two image pickup regions cut out at the image pickup region cut out unit to generate a left side image signal relating to the first region 51 and a right side image signal relating to the second region 52.

Further, the disparity adjusting unit 61 in the image processing unit 32 stores the "disparity information" stored in the ID memory 20 in the endoscope 2 and performs adjustment so that disparity between the left side image signal relating to the first region 51 and the right side image signal relating to the second region 52 becomes substantially zero based on the disparity information under control of the control unit 31.

Still further, the comparing unit 62 compares a luminance value of each pixel in the left side image signal relating to the first region 51 and a luminance value of each pixel in the right side image signal relating to the second region 52 for which the disparity is adjusted to become substantially zero at the disparity adjusting unit 61, for each pixel under control of the control unit 31.

Then, the white spot detecting unit 63 detects whether or not there is a white spot on the image pickup device 25 based on the comparison result of the luminance value for each pixel in the first region 51 and the second region 52 compared at the comparing unit 62 under control of the control unit 31.

The white spot correcting unit 64 performs predetermined correction on the pixel where the white spot occurs to reduce influence of the white spot when the white spot is detected based on the detection result at the white spot detecting unit 63.

Then, the image processing unit 32 outputs a synthesized video signal obtained at the synthesizing unit 65 by performing predetermined 3D synthesis processing on the left side image signal and the right side image signal for which the white spot is corrected at the white spot correcting unit 64 toward the monitor 5.

As described above, according to the endoscope system according to the first embodiment, in the image pickup system which generates a new image for display using two types of images having disparity, it is possible to provide an image pickup system which can detect and correct a white spot pixel accurately.

(Second Embodiment)

A second embodiment of the present invention will be described next.

As described above, while, in the first embodiment, the present invention is applied to an endoscope system including a 3D endoscope which forms two optical images having disparity from each other on one image pickup device as two types of optical images, an endoscope system according to the second embodiment is an endoscope system including an endoscope which forms two optical images generated by separating one incident optical image on one image pickup device.

The endoscope system according to the second embodiment forms the separated two optical images on the image pickup surface of one image pickup device, generates two image pickup signals having different luminance with respect to the two optical images, and acquires a high dynamic range image by converting the two image pickup signals into image signals and synthesizing the image signals.

Figure 7:
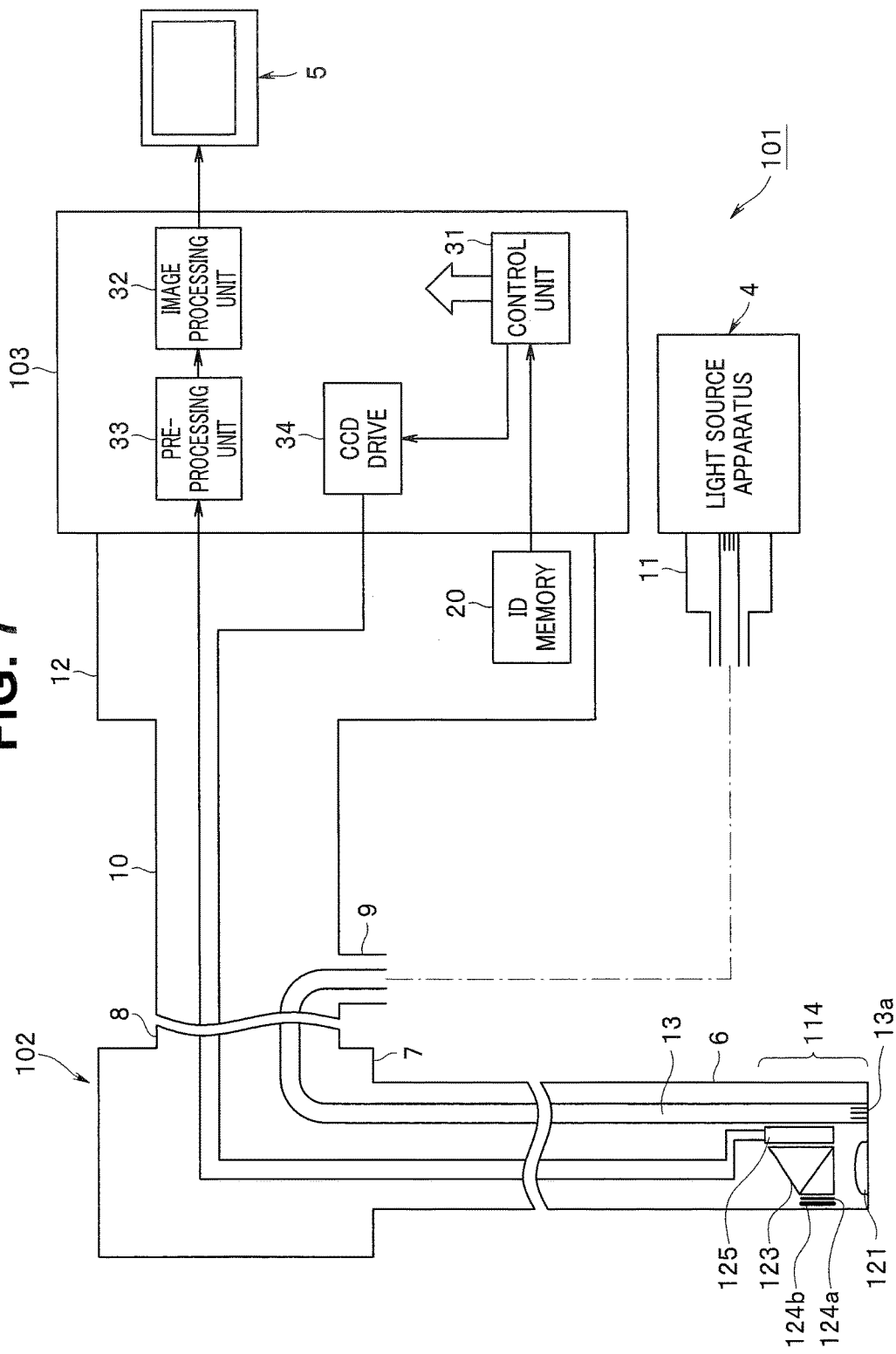
FIG. 7 is a diagram illustrating a configuration of an endoscope system according to a second embodiment of the present invention.
Figure 8:
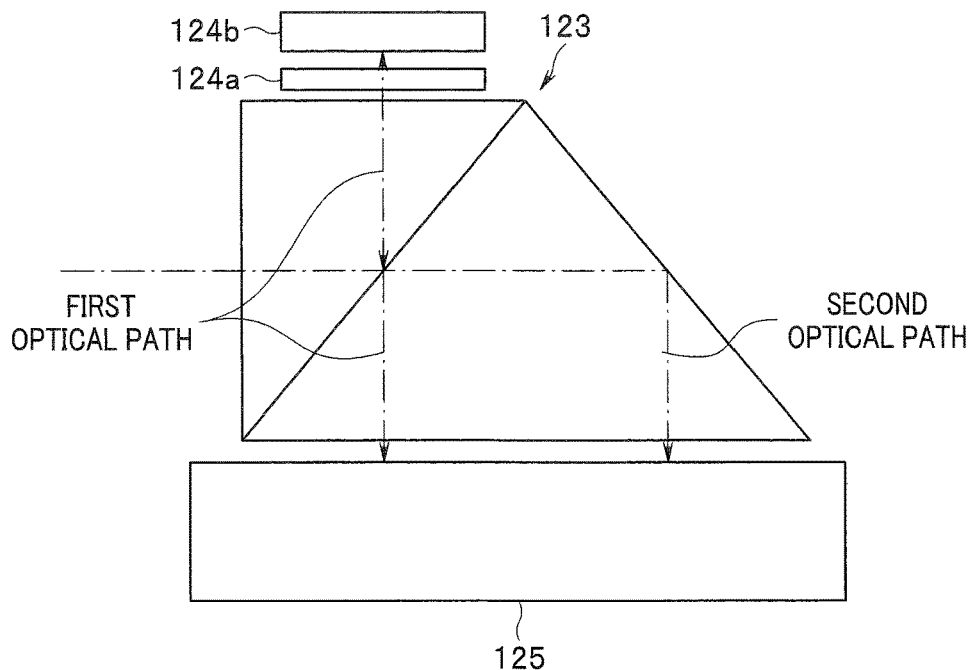
FIG. 8 is a diagram illustrating a configuration of an optical member disposed at a distal end portion of an insertion portion in the endoscope system according to the second embodiment.
Figure 9:
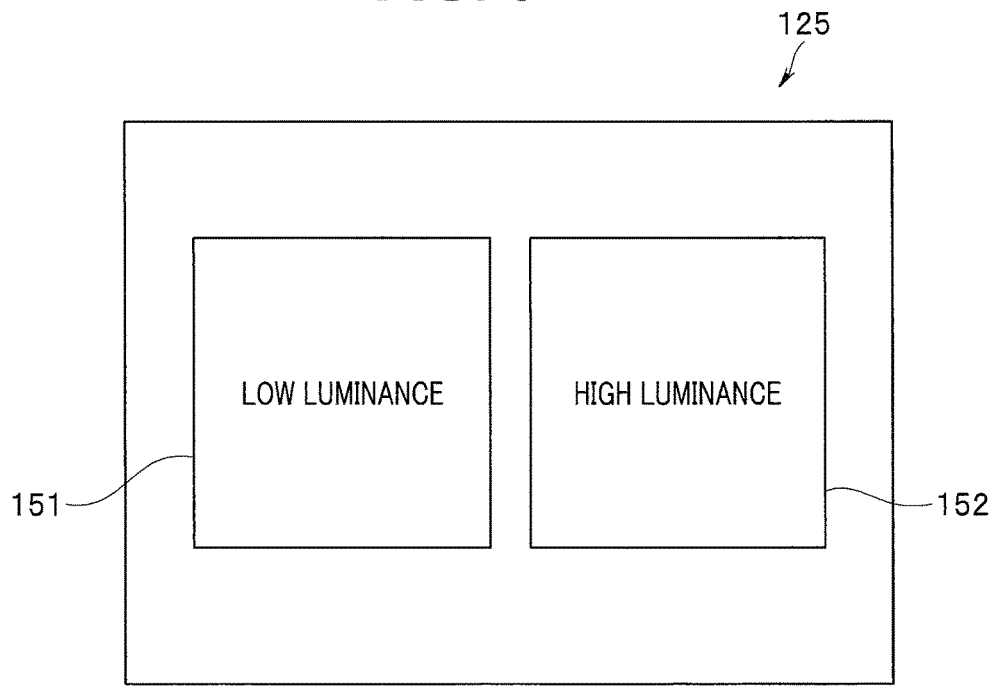
FIG. 9 is a diagram illustrating an example of two types of optical images formed on an image pickup device in the endoscope system according to the second embodiment.

FIG. 7 is a diagram illustrating a configuration of the endoscope system according to the second embodiment of the present invention, FIG. 8 is a diagram illustrating a configuration of an optical member disposed at a distal end portion of an insertion portion in the endoscope system according to the second embodiment, and FIG. 9 is a diagram illustrating an example of two types of optical images formed on the image pickup device in the endoscope system according to the second embodiment.

The endoscope system 101 according to the second embodiment has a similar basic configuration to that of the first embodiment, but a configuration of a distal end portion 114 of an insertion portion at the endoscope 102 is different from that of the first embodiment.

Therefore, here, only part different from that of the first embodiment will be described, and description of the similar part to that of the first embodiment will be omitted.

While in the above-described first embodiment, two objective lenses of the first objective lens 21 and the second objective lens 22 on which images having disparity from each other are incident are disposed, as illustrated in FIG. 7, in the second embodiment, an objective lens 121 on which an optical image of an object such as an affected area is incident is disposed at a distal end portion 114.

Behind the objective lens 121, an optical prism 123 is disposed. As illustrated in FIG. 8, this optical prism 123 is an optical image dividing unit configured to divide the one optical image from the objective lens 121 into a first optical image and a second optical image and emits the divided optical images toward the image pickup device 125. The image pickup device 125 is disposed at image formation positions of the first optical image and the second optical image which are outputted as two optical paths (a first optical path and a second optical path) from the optical prism 123.

On the other hand, in the second embodiment, on a first optical path relating to the first optical image out of the two optical images outputted from the optical prism 123, that is, as illustrated in FIG. 8, on the first optical path in the vicinity of the optical prism 123, relating to the first optical image obtained by reflecting the one optical image at the prism surface, a mirror 124*b* and means for reducing light, for example, an ND filter 124*a* is disposed.

By this means, after the first optical image reflected at the prism surface is incident on the optical prism 123 again by being reflected by the mirror 124*b* while luminance is positively reduced by the ND filter 124*a*, the first optical image is formed at the image pickup device 125.

That is, the first optical image formed at the image pickup device 125 has relatively low luminance compared to the second optical image.

As described above, on the image pickup surface of the image pickup device 125, while the first optical image and the second optical image divided from the one optical image are respectively formed by the optical prism 123, out of these optical images, the first optical image is formed as an image for which luminance is reduced by light reducing means.

Also in the second embodiment, the image pickup device 125 forms two types of optical images of the first optical image and the second optical image in predetermined regions corresponding to the respective optical images on the same image pickup surface of the CCD.

For example, as illustrated in FIG. 9, the first optical image with low luminance is formed in a region 151, and the second optical image with high luminance is formed in a region 152.

Further, also in the second embodiment, as with the first embodiment, for example, in an inspection step of an endoscope manufacturing step, "image formation position information" indicating positions (regions) on the image pickup surface of the image pickup device 125 where the two optical images are formed is acquired in advance through inspection for each endoscope to be shipped, and the "image formation position information" is stored in the ID memory 20 disposed at the connector 12 for signal.

Further, in the second embodiment, concerning the image pickup device 25, "luminance difference information" between the first optical image with low luminance and the second optical image with high luminance is stored in the ID memory 20.

As with the first embodiment, the processor 103 includes a power supply circuit which is configured to generate power supplies of a plurality of power supply voltages required for operation of the image pickup device, or the like, and which is not illustrated, a signal processing circuit (such as an image processing unit 132 and a pre-processing unit 33) configured to perform predetermined signal processing on an image pickup signal outputted from the image pickup device, a CCD drive circuit 34 configured to drive the image pickup device 25 in the endoscope 2, and a control unit 31 configured to control various kinds of circuits including the power supply circuit, the signal processing circuit and the CCD drive circuit 34.

Further, also in the second embodiment, the control unit 31 controls the various kinds of circuits within the processor 103 as described above, and acquires the "image formation position information" and the "luminance difference information" which is individual information of the endoscope 102, stored in the ID memory 20 in the connector 12 for signal when the endoscope 102 is connected to the processor 103.

Further, in the second embodiment, as with the first embodiment, the image processing unit 132 includes an image processing unit which is configured to perform predetermined image processing on the output signal from the pre-processing unit 33, and which is not illustrated, and an image pickup region cut out unit which is configured to cut out predetermined image pickup regions for the first optical image and the second optical image based on the "image formation position information" stored in the ID memory 20 under control of the control unit 31, and which is not illustrated.

The image pickup region cut out unit respectively cuts out a region 151 corresponding to the first optical image and a region 152 corresponding to the second optical image on the image pickup surface based on the "image formation position information" of the first optical image and the second optical image formed on the image pickup surface of the image pickup device 25, which is individual information of the endoscope 102 connected to the processor 103.

The image processing unit 132 performs predetermined image processing respectively in the two image pickup regions (the region 151 and the region 152) cut out at the image pickup region cut out unit to generate two image signals for display (in the present embodiment, a low luminance image signal relating to the region 151 and a high luminance image signal relating to the region 152).

(White Spot Detection and Correction Function in the Second Embodiment)

Further, the image processing unit 132 has a function of detecting a white spot at the image pickup device 125 based on the low luminance image signal relating to the region 151 and the high luminance image signal relating to the region 152 and correcting the white spot.

The white spot detection and correction function in the second embodiment will be described below.

Figure 10:
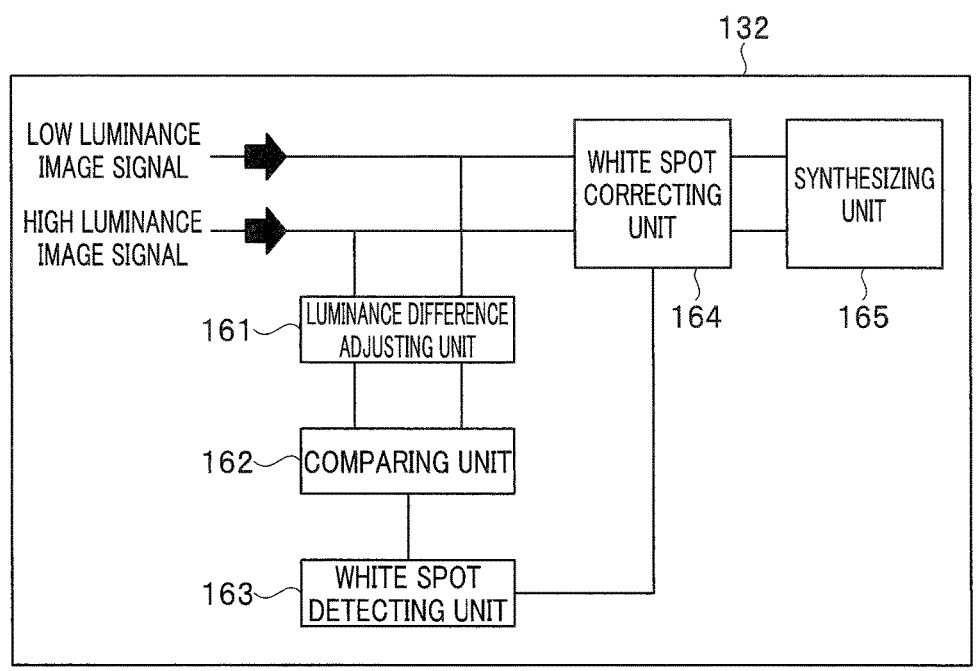
FIG. 10 is a block diagram illustrating a configuration of function units which detect and correct a white spot in an image processing unit of the endoscope system according to the second embodiment.

FIG. 10 is a block diagram illustrating a configuration of function units which detect and correct a white spot at the image processing unit of the endoscope system according to the second embodiment.

As illustrated in FIG. 10, the image processing unit 132 includes a luminance difference adjusting unit 161 configured to adjust a difference of luminance values between the low luminance image signal and the high luminance image signal which are two image signals having different optical characteristics (in the present embodiment, having different luminance values), a comparing unit 162 configured to compare the luminance value between the low luminance image signal and the high luminance image signal adjusted at the luminance difference adjusting unit 161, a white spot detecting unit 163 configured to detect a white spot on the image pickup device 125 based on information compared at the comparing unit 162, and a white spot correcting unit 164 configured to perform predetermined correction on a pixel where the white spot occurs based on the detection result at the white spot detecting unit 163.

The luminance difference adjusting unit 161 stores the "luminance difference information" stored in the ID memory 20 in the endoscope 2 connected to the processor 3 under control of the control unit 31, and performs adjustment based on this luminance difference information so that a luminance difference between the low luminance image signal relating to the region 151 and the high luminance image signal relating to the region 152 having different luminance values becomes substantially zero.

Specifically, in the present embodiment, adjustment is performed so that the luminance difference becomes substantially zero by adjusting a gain relating to the low luminance image signal so as to match the luminance value of the high luminance image signal.

The comparing unit 162 compares for each pixel, a luminance value of each pixel in the low luminance image signal relating to the region 151 and a luminance value of each pixel in the high luminance image signal relating to the region 152, for which the luminance difference is adjusted to be substantially zero at the luminance difference adjusting unit 161, under control of the control unit 31.

The white spot detecting unit 163 detects whether or not there is a white spot on the image pickup device 125 based on the comparison result of the luminance values for each pixel in the region 151 and the region 152 compared at the comparing unit 162, under control of the control unit 31. Because the method for detecting whether or not there is a white spot is the same as that in the first embodiment, detailed description will be omitted here.

Further, as with the first embodiment, the white spot correcting unit 164 performs predetermined correction on a pixel where a white spot occurs based on the detection result at the white spot detecting unit 163 to reduce influence of the white spot. Because this white spot correction method is the same as that in the first embodiment, detailed description will be omitted here.

Returning to FIG. 10, the image processing unit 132 includes a synthesizing unit 615 configured to perform predetermined 3D synthesis processing on the low luminance image signal and the high luminance image signal for which a white spot is corrected at the white spot correcting unit 164 and output the result, and output one video signal subjected to 3D synthesis processing at this synthesizing unit 165 toward the monitor 5.

Operation of the endoscope system according to the second embodiment will be described next.

First, at the endoscope 102, as with the first embodiment, in an inspection step of an endoscope manufacturing step, "image formation position information" indicating positions (regions) on the image pickup surface of the image pickup device 125 where the two optical images are formed is acquired in advance through inspection for each endoscope to be shipped, and the "image formation position information" is stored in the ID memory 20 disposed at the connector 12 for signal.

Further, in the second embodiment, in the inspection step of the endoscope manufacturing step, "luminance difference information" between the first optical image with low luminance and the second optical image with high luminance at the endoscope 102 is stored in the ID memory 20.

Then, at the processor 103, when the endoscope 102 is connected to the processor 103, the control unit 31 acquires the "image formation position information" and the "luminance difference information" stored in the ID memory 20.

On the other hand, at the processor 103, the pre-processing unit 33 receives input of the image pickup signal from the image pickup device 125 and performs predetermined pre-processing, and the image pickup region cut out unit of the image processing unit 132 cuts out predetermined image pickup regions for the first optical image and the second optical image based on the "image formation position information", under control of the control unit 31.

Subsequently, the image processing unit 132 preforms predetermined image processing respectively in the two image pickup regions cut out at the image pickup region cut out unit to generate a low luminance image signal relating to the region 151 and a high luminance image signal relating to the region 152.

Further, the luminance difference adjusting unit 161 in the image processing unit 132 stores the "luminance difference information" stored in the ID memory 20 in the endoscope 102 and performs adjustment so that a luminance difference between the low luminance image signal relating to the region 151 and the high luminance image signal relating to the region 152 becomes substantially zero based on this luminance difference information, under control of the control unit 31.

Further, the comparing unit 162 compares for each pixel a luminance value of each pixel in the low luminance image signal relating to the region 151 and a luminance value of each pixel in the high luminance image signal relating to the region 152 for which the luminance difference is adjusted to be substantially zero at the luminance difference adjusting unit 161, under control of the control unit 31.

After this, the white spot detecting unit 163 detects whether or not there is a white spot on the image pickup device 125 based on the comparison result of the luminance values for each pixel in the region 151 and the region 152 compared at the comparing unit 162, under control of the control unit 31.

When the white spot is detected, the white spot correcting unit 164 performs predetermined correction on the pixel where the white spot occurs based on the detection result at the white spot detecting unit 163 to reduce influence of the white spot.

Then, the image processing unit 132 performs predetermined 3D synthesis processing on the low luminance image signal and the high luminance image signal for which the white spot is corrected by the white spot correcting unit 164 at the synthesizing unit 165 and outputs the synthesized video signal toward the monitor 5.

As described above, according to the endoscope system according to the second embodiment, in an image pickup system which generates a new image for display using two types of images having different luminance values, it is possible to provide an image pickup system which can detect and correct a white spot pixel accurately.

The present invention can be applied not only to an endoscope system having an endoscope on which a solid-state image pickup device as in the first embodiment and the second embodiment is mounted, but can be applied to an image pickup system including a solid-state image pickup device, which can generate a new image for display using two types of images and detect a white spot pixel.

The present invention is not limited to the above-described embodiments, and various changes, modifications, or the like, are possible within the gist of the present invention.

What is claimed is:

1. An image pickup system comprising:
    an image pickup sensor configured to pick up an optical image of an object;
    an optical system configured to:
        generate a first optical image of the object and a second optical image having optical characteristic disparity from the first optical image; and
        form the first optical image and the second optical image at predetermined positions on the image pickup sensor;
    a memory configured to store in advance image formation position information of the first optical image and the second optical image on an image pickup surface of the image pickup sensor and information indicating an amount of optical characteristic disparity of the first optical image and the second optical image;
    a processor comprising hardware configured to:
        perform photoelectric conversion on the first optical image and the second optical image formed on the image pickup sensor to respectively output the first optical image and the second optical image as a first image pickup signal and a second image pickup signal; and
        generate a first image signal and a second image signal for display by respectively cutting out a first region corresponding to the first optical image and a second region corresponding to the second optical image on the image pickup surface based on the image formation position information,
        set a pair of pixel positions indicating corresponding regions of the first image signal and the second image signal based on the information indicating the amount of optical characteristic disparity;
        compare luminance values of respective pixels in the first image signal and the second image signal based on the setting of the pair of pixel positions; and
        detect a pixel defect based on a comparison result of the luminance values.

2. The image pickup system according to claim 1, wherein the processor is further configured to:
    detect a luminance excess pixel having a greater luminance value in the pair of pixels for which a difference of luminance values is equal to or greater than a predetermined value as the pixel defect based on the comparison result of the luminance value comparing unit, and correct the detected luminance excess pixel so that the difference of the luminance values become equal to or less than the predetermined value; and synthesize the first image signal and the second image signal subjected to the correction and output a synthesized signal.

3. The image pickup system according to claim 2, comprising:

an endoscope including the image pickup sensor, the optical system, the processor, and the memory.

* * * * *